(12) United States Patent
Pearlstein et al.

(10) Patent No.: US 7,244,839 B2
(45) Date of Patent: Jul. 17, 2007

(54) MAIZE STARCH CONTAINING ELEVATED AMOUNTS OF ACTUAL AMYLOSE

(75) Inventors: Richard W. Pearlstein, Newark, DE (US); Karen E. Broglie, Landenberg, PA (US); Christopher F. Hines, Middletown, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 456 days.

(21) Appl. No.: 10/397,954

(22) Filed: Mar. 26, 2003

(65) Prior Publication Data

US 2003/0221220 A1 Nov. 27, 2003

Related U.S. Application Data

(60) Provisional application No. 60/368,387, filed on Mar. 27, 2002, provisional application No. 60/381,534, filed on May 15, 2002.

(51) Int. Cl.
*C08B 31/00* (2006.01)
*C08B 33/00* (2006.01)
*C08B 35/00* (2006.01)
*C07H 19/00* (2006.01)
*C07H 21/00* (2006.01)

(52) U.S. Cl. ............... 536/102; 536/105; 536/107; 536/108; 536/111; 536/115; 536/120; 536/124

(58) Field of Classification Search ............... 536/102, 536/105, 106, 107, 108, 111, 115, 120, 124
See application file for complete search history.

(56) References Cited

U.S. PATENT DOCUMENTS

| | | | |
|---|---|---|---|
| 5,107,065 A | 4/1992 | Shewmaker et al. | |
| 5,231,020 A | 7/1993 | Jorgensen et al. | |
| 5,300,145 A * | 4/1994 | Fergason et al. | 536/102 |
| 5,977,454 A | 11/1999 | McNaught et al. | |
| 6,326,045 B1 | 12/2001 | Rubio et al. | |

FOREIGN PATENT DOCUMENTS

| | | |
|---|---|---|
| WO | WO 94/09144 A1 | 4/1994 |
| WO | WO 97/22703 A2 | 6/1997 |
| WO | WO 00/06755 A2 | 2/2000 |
| WO | WO 01/12782 A2 | 2/2001 |
| WO | WO 01/19975 A2 | 3/2001 |

OTHER PUBLICATIONS

Rendleman et al. Biotechnol. Appl. Biochem. (2000), vol. 31, pp. 171-178.*
Richardson et al. MRS Bulletin, Dec. 2000, pp. 20-24.*
Whistler, Bemiler & Paschall in Starch: Chemistry and Technology, 1984, p. 54.
Paul H. Richardson et al., High-Amylose Starches: From Biosynthesis to Their Use as Food Ingredients, MRS Bulletin, Dec. 2000, pp. 20-24.
Ming Gao et al., Evolutionary conservation and expression patterns of maize starch branching enzyme I and IIb genes suggests isoform specialization, Plant Molecular Biology, 30:1223-1232, 1996.
Charles D. Boyer et al., Evidence for Independent Genetic Control of the Multiple Forms of Maize Endosperm Branching Enzymes and Starch Synthases, Plant Phys., 1981, vol. 67:1141-1145.
J. D. Klucinec et al., Fractions of High-Amylose Starches Obtained by Differential Alcohol Complexation, 1997, AACC Annual Meeting, 223.168.
Yasuhito Takeda et al., Branching of amylose by the branching isoenzymes of maize endosperm, Carbohydrate Research, 240(1993):253-263.
Tadashi Baba et al., Sequence Conservation of the Catalytic Regions of Amylolytic Enzymes in Maize Branching Enzyme-I, Biochemical and Biophysical Research Communications, vol. 181(1):87-94, 1991.
Alan M. Myers et al., Recent Progress toward Understanding Biosynthesis of the Amylopectin Crystal, Plant Phys., vol. 122:989-997, Apr. 2000.
Han Ping Guan et al., Differentiation of the Properties of the Branching Isoenzymes from Maize (Zea mays), Plant Phys., vol. 102:1269-1273, 1993.
Ming Gao et al., Independent Genetic Control of Maize Starch-Branching Enzymes IIa and IIb, Plant Phys., vol. 114:69-78, 1997.
C. Gerard et al., Amylose determination in genetically modified starches, Carbohydrate Polymers, vol. 44:19-27, 2001.
Yong-Cheng Shi et al., Molecular Structure of a Low-Amylopectin Starch and Other High-Amylose Maize Starches, Journal of Cereal Science, vol. 27:289-299, 1998.
Dane K. Fisher et al., Starch Branching Enzyme II from Maize Endosperm, Plant Phys., vol. 102:1045-1046, 1993.
Dane K. Fisher et al., A cDNA Encoding Starch Branching Enzyme I from Maize Endosperm, Plant Phys., vol. 108:1313-1314, 1995.
Kyung-Nam Kim et al., Genomic organization and promoter activity of the maize starch branching enzyme I gene, Gene, vol. 216:233-243, 1998.
Kyung-Name Kim et al., Molecular Cloning and characterization of the Amylose-Extender gene encoding starch branching enzyme IIB in maize, Plant Molecular Biology, vol. 38:945-956, 1998.
A. M. Smith et al., The Synthesis of the Starch Granule, Annu. Rev. Plant Phys. Plant Mol. Biol., vol. 48:67-87, 1997.
Gerhard P. Schwall et al., Production of very-high-amylose potato starch by inhibition of SBE A and B, Nature Biotechnology, vol. 18:551-554, May 2000.
Ming Gao et al., Characterization of dull1, a Maize Gene Coding for a Novel Starch Synthase, The Plant Cell, vol. 10:339-412, Mar. 1998.
Susan L. Blauth et al., Identification of Mutator Insertional Mutants of Starch-Branching Enzyme 2a in Corn, Plant Phys., vol. 125:1396-1405, Mar. 2001.
Paul H. Richardson et al., High-Amylose Starches: From Biosynthesis to Their Use as Food Ingredients, MRS Bulletin, pp. 20-24, Dec. 2000.
Jacob A. Rendleman, Jr., Hydrolytic action of α-amylose starch of low mulecular mass, Biotechnol. Appl. Biochem, 31:171-178, 2000.

* cited by examiner

*Primary Examiner*—Patrick Lewis

(57) ABSTRACT

The present invention is directed to a starch comprising a novel percentage of actual amylose. A grain comprising the starch is also embodied by the present invention. The present invention is also directed to a plant comprising the novel starch.

18 Claims, 7 Drawing Sheets

MAIZE STARCH CONTAINING ELEVATED AMOUNTS OF ACTUAL AMYLOSE

This application claims the benefit of U.S. Provisional Application No. 60/368,387, filed Mar. 27, 2002 and U.S. Provisional Application No. 60/381,534, filed May 15, 2002.

FIELD OF THE INVENTION

This invention concerns a maize (corn) starch having a high percentage of amylose. The corn starch is derived from transgenic plants suppressed in the expression of at least two SBE isoforms. This invention also includes the transgenic plants and their progeny and grains producing such a starch.

BACKGROUND OF THE INVENTION

The major carbohydrates found in vascular plants are sucrose, starch, cellulose and fructans. Sucrose is most commonly purified from sucrose-producing plants and used as a sweetener. Starch and cellulose are currently used in numerous food and non-food applications in their native form or after chemical modification or hydrolysis. Fructans have commercial applications in the industrial, medical, food and feed industries.

Starch is a mixture of two polysaccharides, amylose and amylopectin. Amylose is an unbranched chain of up to several thousand $\alpha$-D-glucopyranose units linked by $\alpha$-1,4 glycosidic bonds. Amylopectin is a highly branched molecule of up to 50,000 $\alpha$-D-glucopyranose residues linked by $\alpha$-1,4 and $\alpha$-1,6 glycosidic bonds. Approximately 5% of the glycosidic linkages in amylopectin are $\alpha$-1,6 bonds, which leads to the branched structure of the polymer.

Amylose and amylopectin molecules are organized into granules that are stored in photosynthetic tissues during light periods or in storage organs. The ratio of amylose to amylopectin and the degree of branching of amylopectin affect the physical and functional properties of the starch. Functional properties, such as viscosity and stability of a gelatinized starch, determine the usefulness and value of starches in food and industrial applications. Currently, specific functional properties are met by using starches obtained from various crops such as corn, rice, or potatoes or by chemically modifying the starch. Various types and degrees of chemical modification are used in the starch industry, and the labeling and use of chemically modified starches must meet government regulations.

Biosynthesis of starch is thought to occur through the action of four enzymes, ADP glucose pyrophosphorylase (EC 2.7.7.27), starch synthase (EC 2.4.1.21), starch branching enzyme (EC 2.4.1.18), and debranching enzyme (EC 2.4.1.41) [for reviews, see Smith, A. M., Denyer, K., and Martin, C. (1997) *Annu. Rev. Plant Physiol. Plant Mol. Biol.* 48:67-87; Myers, A. M. et al. (2000) *Plant Phys.* 122:989-997]. ADP glucose pyrophosphorylase catalyzes the synthesis of ADP glucose, the substrate for the synthesis of starch polymers. This enzyme is formed from a small and a large subunit. Most plants contain small multigene families of one or both of these subunits and in most cases various members of the family are differentially expressed in the plant organs. Starch synthase (SS), as its name implies, catalyzes the formation of $\alpha$-1,4-linked glucose polymers from ADP-glucose. All plants possess granule bound starch synthases (GBSS) and most contain soluble starch synthases (SSI, SSII, SSIII). Branching enzymes (SBEs) catalyze the formation of amylopectin branch points by cleaving the $\alpha$-1,4 linkages and creating new $\alpha$-1,6 bonds. At least three SBE isoforms have been identified in maize. Debranching enzymes (DBEs) catalyze the hydrolysis of $\alpha$-1,4 linkages and multiple isoforms have been found in all plants studied.

The proportion of amylose to amylopectin and the degree of branching of amylopectin are under genetic control. Differences in the degree of starch branching or polymerization are known to result in a change in the physiochemical properties of starch. Due to its unique functional properties, starch with high levels of amylose is in great demand in industry where high-amylose starches are high-value specialty products. These starches are very useful for industrial products because they form gels with high strength and have superior barrier and film-forming properties. In food uses, high-amylose starches readily form firm gels useful in confectionery products and contain resistant starch, which provides ingestible dietary fiber and is useful in low calorie food applications. Commercially available high-amylose starches from maize are extracted from grain containing the recessive ae mutation and are available in 2 classes. Class V is known as "50% amylose" and is sold under brand names such as Hylon® V and Gelose 50. Class VII is known as "70% amylose" and is sold under brand names such as Hylon® VII and Gelose 70.

In the last decade or so molecular genetic methods have been utilized to obtain plants producing starches with different ratios of amylose to amylopectin. In PCT publication No. WO 94/09144 (published 15 Jan. 1994) it is suggested that the use of sense and antisense transgenes may be used to alter the natural ratios of different starch synthase and branching enzymes in the recipient plant. This publication does not disclose any specific examples in which the starch characteristics were actually modified. PCT publication No. WO 00/06755 (published 10 Feb. 2000) shows the results of expressing all or a portion of a corn SBE isoform in sense or antisense orientation in transgenic corn. The resulting plants produce starches with higher levels of amylose and increased molecular weight of the amylose component together with shorter amylopectin chains than the non-transformed plants. Transgenic potato plants expressing, simultaneously, antisense versions of two potato SBE isoforms produce very-high-amylose starch (Schwall, G.P. et al. (2000) *Nature Biotech.* 18:551-554.

Alteration of starch fine structure in corn is complicated by the fact that three isoforms exhibiting starch branching enzyme activity have been identified in corn endosperm: SBEI, SBEIIa and SBEIIb. In the amylose extender (ae) mutant, SBEIIb activity is found to be deficient while in the dull (du) mutant, decreased levels of SBEIIa are observed (Boyer, C. D. and Preiss, J. (1981) *Plant Physiol.* 67:1141-1145). Later work has shown that the primary lesion in the dull mutation is a soluble starch synthase and deficiencies in this enzyme are responsible for the reduction in SBE (Gao, M. et al. (1998) *Plant Cell* 10:399-412). Studies of the catalytic properties of the corn starch branching enzymes indicate that the isoforms differ in substrate preference and in the length of glucan chain that is transferred. SBEI activity is higher when amylose serves as the substrate, and longer chains are preferentially transferred. The SBEII isoforms display higher activity with more highly branched substrates such as amylopectin. These enzymes preferentially transfer shorter glucan chains (Guan, H. and Preiss, J. (1993) *Plant Physiol.* 102:1269-1273; Takeda, Y. et al. (1993) *Carbohydrate Res.* 240:253-263). There is further evidence that the corn SBE isoforms are distinguished not only by their catalytic properties, but also by their pattern of expression in different corn tissues and in corn endosperm during development (Gao, M. et al. (1996) *Plant Mol. Biol.* 30:1223-1232; Gao, M. et al. (1997) *Plant Physiol.* 114:69-78).

By applying techniques of molecular biology, it has been possible to gain a better understanding of the role of individual SBE isoforms in starch biosynthesis and to generate unique starch phenotypes. An SBEIIa mutant obtained by Mutator insertional inactivation has recently been described. Endosperm starch isolated from this mutant lacks detectable SBEIIa and shows no change in amylopectin branch chain distribution. The amylose amounts were not reported in this study and no mention is made of the effect of combining the SBEIIa mutation with loss of either SBEI or SBEIIb (Blauth, S. L. et al. (2001) *Plant Physiol.* 125:1396-1405). Inhibition of SBEI expression alone produces no significant change in amylopectin structure or amylose content in corn starch. However, antisense inhibition of SBEI can be combined with the deficiency of SBEIIb in the ae mutant to generate an actual amylose level of about 50%, PCT publication WO 97/22703. This is compared to the actual amylose level of about 24% found in dent starch. The term "actual amylose" is defined below.

The measurement of amylose has long been a technical issue in the literature, and different measurement methods give remarkably differing results. The 50% amylose content of Class V starches and the 70% amylose content of Class VII starches is measured by iodine binding methods, which tend to overestimate the amount of amylose. For example, the double mutant amylose extender-waxy (aewx) starch from maize shows an amylose content of 15-26% when measured using the iodine binding method (Whistler, BeMiler, & Paschall in *Starch: Chemistry and Technology* 1984, p. 54). The overestimation in this method is made obvious because, in fact, this starch contains no amylose at all; all waxy starches lack all amylose as the waxy mutation results in a complete absence of functional granule bound starch synthase, the enzyme long known to be responsible for amylose biosynthesis.

An exception to the problem of overestimation of amylose levels using the iodine method are those of dent (wild type) starch and other normal or low amylose starches. The reason for this is simply that dent starch is used as a standard in these assays. The standards used for the calibration curve in these assays is prepared from dent and/or low amylose starches, which have an amylose content of about 23% to about 25%. With increasing amounts of amylose above that found in dent, the overestimation of amylose increases. This is due to mathematical reasons based on the use of dent starch as a standard and changes in amylopectin structure as an effect of branching enzyme inhibition, longer amylopectin chains are also formed and bind iodine, increasing apparent amylose.

The limitations of the old technique of amylose determination by iodine binding has long been recognized, and several other analytical methods have been proposed as superior. Fractionation of dispersed starch using differential precipitation by such solvents as thymol, n-butanol and/or isoamyl alcohol has been used both to prepare purified amylose and amylopectin, and to determine the amylose content of the starch. As is typical of most precipitation methods, absolute separations are very difficult to achieve. This technique also neglects the existence of 'intermediate material' which is present in significant amounts, especially in high amylose starches. (Klucinec, J. D. and Thompson, D. B. (1997) AACC Annual Meeting 223.163). This material is branched, and behaves in a similar manner to amylopectin in alcohol precipitation experiments, however it has been erroneously added to the amylose fraction in the past, again overestimating the amylose content. Other proposed techniques include Con A lectin precipitation, DSC determination of amylose-lipid binding, and size exclusion chromatography (SEC), using either native starch or starch debranched with isoamylase. With the sole exception of SEC of debranched starch these methods all give rise to overestimates of amylose content (Gerard, C. et al. (2001) *Carbohydr. Polym.* 44:19-27). While native starch GPC could theoretically be accurate, the difficulty in keeping the amylopectin in solution and its large radius of gyration makes this assay fraught with problems. Most practitioners of this method can recover only a small, non-representative proportion of the starting material from the column, particularly when sample preparation steps such as filtration (with pore size less than 5μ) or centrifugation are used. If the temperature and DMSO content of the mobile phase is not kept high throughout the sample preparation and chromatography steps, differential precipitation will distort the results.

A more practical, and accurate, method to measure the amylose content of starch is gel permeation chromatography (GPC) following enzymatic debranching of the amylopectin in the gelatinized starch. This allows complete loading of all carbohydrates from the starch, and quantitative recovery from the chromatography system. Values of amylose obtained in this fashion are referred to herein as "actual amylose." Using this system, Class V starches ("50% amylose" by iodine methods) contain about 34% actual amylose and Class VII starches ("70% amylose" by iodine methods) contain about 42% actual amylose (whereas wild-type dent starches contain about 23-25% amylose). The starch of the present invention has an actual amylose level of at least about 76%.

SUMMARY OF THE INVENTION

The present invention is directed to a substantially pure corn starch comprising at least about 76% actual amylose.

Another embodiment of the present invention is a substantially pure corn starch extracted from a corn plant source, wherein the starch comprises at least about 76% actual amylose, the corn plant source comprising at least one recombinant DNA molecule comprising at least a portion of corn starch branching enzymes I and II, the molecule sufficient to suppress the endogenous expression of corn starch branching enzymes I and II, or any progeny thereof, wherein the progeny comprise the molecule. The recombinant DNA molecule may comprise a first molecule comprising at least a portion of starch branching enzyme I and a second molecule comprising at least a portion of starch branching enzyme II. Alternatively, the recombinant DNA molecule may comprise at least a portion of starch branching enzyme I and at least a portion of starch branching enzyme II.

Another embodiment of the present invention is a corn plant comprising a recombinant DNA molecule capable of suppressing corn starch branching enzymes I and II.

Yet another embodiment of the present invention is a corn kernel or a corn plant comprising the starch of the present invention.

In addition, the present invention is directed to flour produced from the starch of the present invention.

BRIEF DESCRIPTION OF THE FIGURES AND SEQUENCE LISTING

The invention can be more fully understood from the following detailed description and the accompanying Figures and Sequence Listing which form part of this application.

FIG. 1 shows a diagram of plasmid pBE122. This plasmid contains three pieces of the SBEIIb gene under the control of the 27 kD zein promoter and a 960 bp fragment of the 10 kD zein 3' end. A modified SBEIIb region was assembled with nucleotides 91-1105 and 1453-2177 in sense orientation with respect to the promoter and nucleotides 91-784 in antisense orientation with respect to the promoter.

FIG. 2 shows a diagram of plasmid pBE117. This plasmid contains three pieces of the SBEI gene under the control of the 27 kD zein promoter and a 960 bp fragment of the 10 kD zein 3' end. A modified SBEI region was assembled with nucleotides 18-698 and 1221-2390 in sense orientation with respect to the promoter and nucleotides 18-698 in antisense orientation with respect to the promoter.

Figure 1:
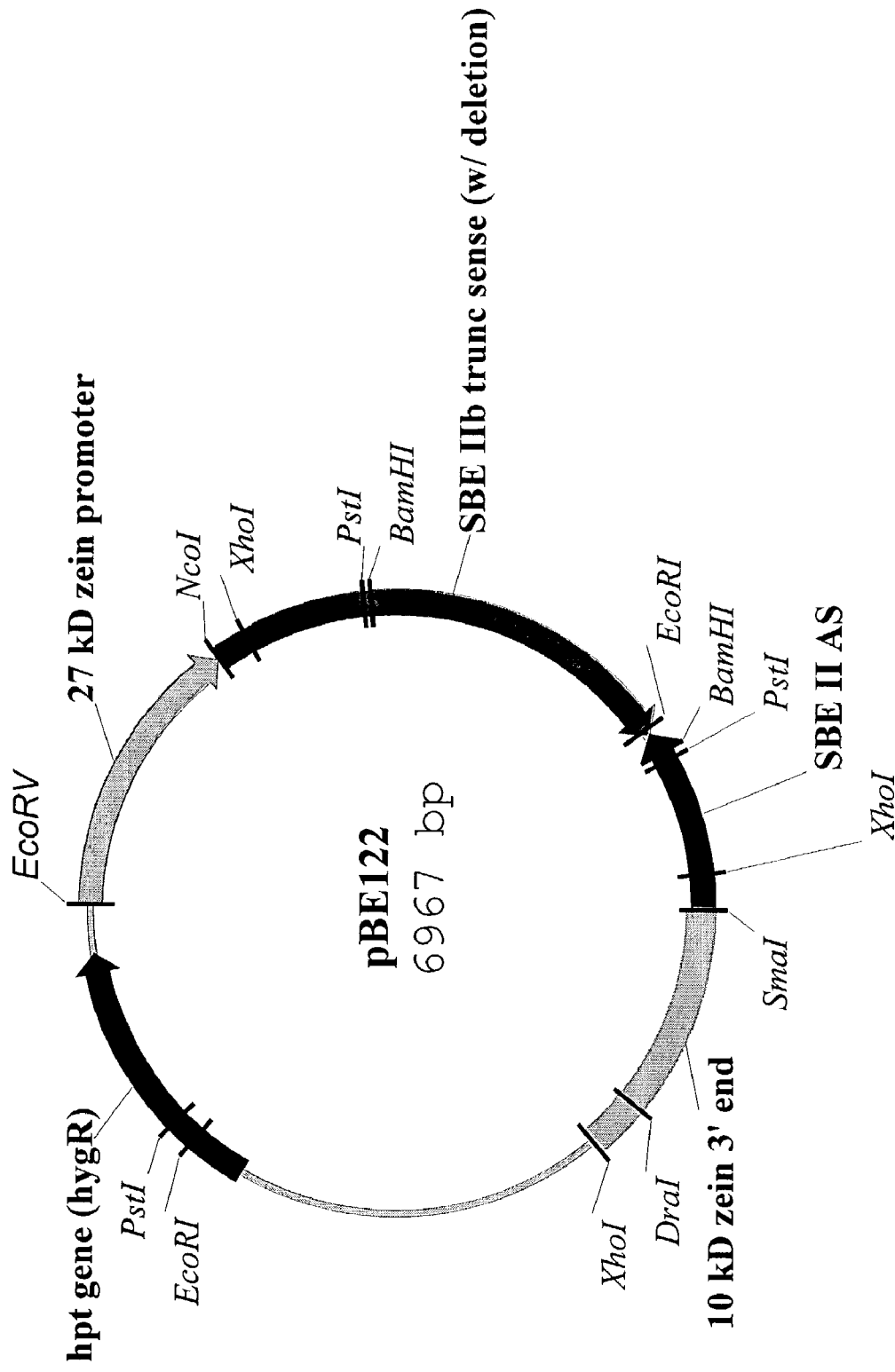

The following sequence descriptions and the Sequence Listing attached hereto comply with the rules governing nucleotide and/or amino acid sequence disclosures in patent applications as set forth in 37 C.F.R. §1.821-1.825.

SEQ ID NO:1 is the nucleotide sequence comprising the cDNA insert corresponding to the modified SBEIIb region in pBE122.

SEQ ID NO:2 is the nucleotide sequence comprising the cDNA insert corresponding to the modified SBEI region in pBE117.

SEQ ID NO:3 is the nucleotide sequence of the oligonucleotide primer 110A used for identification of plants containing plasmid pBE117.

SEQ ID NO:4 is the nucleotide sequence of the oligonucleotide primer 110B used for identification of plants containing plasmid pBE117.

SEQ ID NO:5 is the nucleotide sequence of the oligonucleotide primer 95A used for identification of plants containing plasmid pBE122.

SEQ ID NO:6 is the nucleotide sequence of the oligonucleotide primer 95B used for identification of plants containing plasmid pBE122.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

Definitions

In the context of this disclosure, a number of terms should be utilized.

The term "corn" refers to *Zea mays*, and is used herein interchangeably with maize. In accordance with the present invention, corn plant sources may be the plant per se. In addition, the corn plant source of the subject invention includes and is not limited to the seed, also used herein interchangeably with kernel and grain, plant cells, plant protoplasts, plant cell tissue culture from which corn plants can be regenerated, plant calli, plant clumps, and plant cells that are intact in plants or parts of plants such as embryos, pollen, flowers, ears, cobs, leaves, husks, stalks, roots, root tips, anthers, silk and the like. The preferred corn of the present invention exhibits suppression of starch branching enzymes I and II.

The term "starch" refers to a polysaccharide consisting of α-D-(1,4) glucan that may contain a variable proportion of α-D-(1,6) branches. As used herein, the term "starch fine structure" refers to the molecular structure of a starch polymer, the presence, abundance and distribution of α-D-(1,6) bonds and the presence, abundance and length of both branched and unbranched α-D-(1,4) glucans in the polymer. Starch fine structure is described by the percent actual amylose present in the starch, the amylopectin branch chain distribution, or by the relative proportion of amylose to amylopectin, or by the degree of polymerization of amylose. Alteration of any of these structural molecular components results in an altered starch fine structure. One, two or all three of these parameters may be altered independently of one another. The term "degree of polymerization" refers to the number of α-D-glucopyranose units in a molecule or designated portion of a molecule such as a branch chain of amylopectin.

The term "actual amylose" refers to the relative amylose content obtained by using gel permeation chromatography (GPC) after enzymatic debranching of the amylopectin in the gelatinized starch. This allows complete loading of all carbohydrates from the starch, and quantitative recovery from the chromatography system. The principle of this two step process, which measures the proportion of amylose to amylopectin in the starch and elucidates some of the amylopectin fine-structure, is as follows. First the starch is gelatinized (such as by cooking, for example) in an excess amount of water which swells and ruptures the crystalline starch granules and disperses the granule contents in the water. After cooling, an enzyme is added (isoamylase, for example) which attacks the chemical bonds at the branch-points in the starch. Since amylopectin primarily contains these branch-points, the amylose is barely changed by this step while the amylopectin is extensively degraded into much smaller fragments. Upon fractionating the mixture on the basis of fragment size, the relative amounts of the different size classes of those fragments can be used to estimate the fine-structure of the original amylopectin molecule. In addition, since the amylose is not significantly altered by the enzymatic treatment, it comprises the fraction of starch with the largest fragment size. The relative amounts of amylose and amylopectin can be derived from the same data upon fractionation. Size fractionation is accomplished by subjecting the complete mixture to gel permeation chromatography (GPC). GPC separates molecules based on their size in solution. Schematically described, the molecules are passed through a column packed with polymer beads riddled with microscopic pores. These pores are made with defined average diameters, and by selecting the appropriate mixture of pore sizes, molecules of various size ranges can be separated. This occurs because the smallest molecules tend to become trapped longest in the pores and thus have a very long effective path through the column, while the largest fit into very few pores and thus pass through the column more rapidly, going around most of the beads and emerging first. By measuring the material eluting from the column over time compared with standards of known size, the composition of the experimental mixture based on size is determined.

Using this system, Class V starches ("50% amylose" by iodine methods) contain about 34% actual amylose and Class VII starches ("70% amylose" by iodine methods) contain about 42% actual amylose (whereas wild-type dent starches contain about 23-25% amylose). The starch of the present invention has an actual amylose level of at least about 76% in accordance gel permeation chromatography. The amount of amylose measured by iodine binding is, in most cases, overestimated due to interference of long amylopectin chains and it can be underestimated due to the presence of low molecular weight linear molecules. The use of GPC after debranching is now the preferred method of measuring amylose content (Shi, Y-C et al. (1998) *J. Cereal Sci.* 27:289-299). True or accurate amylose may be used interchangeably herein with actual amylose.

As used herein, the term "branch chain distribution" refers to the distribution of α-1,4-linked glucan chains which is detected following isoamylase digestion of amylopectin and subsequent fractionation of the liberated branches by size exclusion chromatography.

As used herein, "substantially pure" refers to corn starch having most preferably 100% actual amylose, thus being substantially free of impurities. The corn starch of the present invention comprises at least about 76% actual amylose. Preferably, the corn starch of the present invention comprises about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% actual amylose. Thus a typical range of actual amylose is from about 85% to about 90% actual amylose, about 80% to about 95%, about 76% to about 99% actual amylose.

The term "flour" as used herein comprises a finely ground corn grain. Flour may be ground by sifting or milling, for example, such that the fine mealy parts of grain are separated from the fibrous bran covering on the grain. Flour may be used interchangeably herein with meal, such as cornmeal. Flour may be prepared by wet milling, the multi-step process for separating corn into its component parts. Starch is the main product of the wet milling process with protein (gluten), fiber, and oil as by-products. Flour may be prepared for example in accordance with the method set forth in U.S. Pat. No. 6,326,045.

The term "recombinant DNA molecule" is used herein to refer to a combination of nucleic acid sequences of different origin that are operably linked and that can, upon becoming integrated into a cell, replicate either autonomously or with the assistance of the cell. Recombinant DNA may contain a variety of sequences such as and not limited to one or more of the following: coding sequence, regulatory sequences such as for example, promoter and intron, terminator. Accordingly, in accordance with the present invention, the recombinant DNA molecule may comprise for example, a promoter, a starch branching enzyme I sequence, a starch branching enzyme II sequence and a terminator. Another embodiment results in a recombinant DNA molecule that may comprise for example, a promoter, a starch branching enzyme I sequence, a terminator, a promoter, a starch branching enzyme II sequence and a terminator. Yet another embodiment of the present invention may comprise for example, a first recombinant DNA molecule comprising a promoter, a starch branching enzyme I sequence and a terminator and a second recombinant DNA molecule comprising a promoter, a starch branching enzyme II sequence and a terminator. Thus, in accordance with the present invention, the recombinant DNA molecule may comprise a transgene. A recombinant DNA molecule may be introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed in most cell types at most times are commonly referred to as "constitutive promoters". New promoters of various types useful in plant cells are constantly being discovered; numerous examples may be found in the compilation by Okamuro, J. K. and Goldberg, R. B. (1989) *Biochemistry of Plants* 15:1-82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L. et al., (1989) *Plant Cell* 1:671-680.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

As used herein, "substantially similar" refers to polynucleotides, genes, coding sequences, and the like, wherein changes in one or more nucleotide bases results in substitution of one or more amino acids, but do not affect the functional properties of the polypeptide encoded by the nucleotide sequence. "Substantially similar" also refers to polynucleotides wherein changes in one or more nucleotide bases does not affect the ability of the polynucleotide to mediate alteration of gene expression by gene silencing through for example antisense or co-suppression technology. "Substantially similar" also refers to modifications of the polynucleotide of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar polynucleotides may be selected by screening polynucleotides representing subfragments or modifications of the polynucleotides of the instant invention, wherein one or more nucleotides are substituted, deleted and/or inserted, for their ability to affect the level of the polypeptide encoded by the unmodified polynucleotides in a plant or plant cell. For example, a substantially similar polynucleotides representing at least one of 30 contiguous nucleotides derived from the instant polynucleotides can be constructed and introduced into a plant or plant cell. The level of the polypeptide encoded by the unmodified polynucleotides present in a plant or plant cell exposed to substantially similar polynucleotide can then be compared to the level of the polypeptide in a plant or plant cell that is not exposed to the substantially similar polynucleotides.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by a cell. "cDNA" refers to a DNA that is complementary to and synthesized from an mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment or recombinant DNA molecule so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

"Transformation" refers to the transfer of a nucleic acid fragment or recombinant DNA molecule into the genome of a host organism. "Stable transformation" refers to the transfer of a nucleic acid fragment or recombinant DNA molecule into a genome of a host organism, including both nuclear and organellar genomes, resulting in genetically stable inheritance. In contrast, "transient transformation" refers to the transfer of a nucleic acid fragment or recombinant DNA molecule into the nucleus, or DNA-containing organelle, of a host organism resulting in gene expression without integration or stable inheritance. Host organisms containing the transformed nucleic acid fragments or recombinant DNA molecules are referred to as "transgenic" organisms. The preferred method of cell transformation of rice, corn and other monocots is the use of particle-accelerated or "gene gun" transformation technology (Klein, T. M. et al. (1987) *Nature* (London) 327:70-73; U.S. Pat. No. 4,945,050), or an *Agrobacterium*-mediated method using an appropriate Ti plasmid containing the transgene (Ishida, Y. et al. (1996) *Nature Biotech.* 14:745-750).

"PCR" amplification or "Polymerase Chain Reaction" is a technique for the synthesis of large quantities of specific DNA segments that consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Corn is used as human food, livestock feed and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch from the wet-milling industry and corn flour from the dry-milling industry. The industrial applications of corn starch and flour are based on functional properties, and ability to suspend particles. The corn starch and flour have application in the paper and textile industries. Other industrial uses include applications in adhesives, building materials, foundry binders, laundry starches, explosives, oil-well muds, and other mining applications.

High amylose starch is useful in applications that involve film-forming ability, higher gel strength, greater water resistance, and higher cooking temperature. Examples include and are not limited to improved starch-based corrugating adhesives, such as described in Leake et al. (U.S. Pat. No. 5,405,437), used in corrugated boxes, food products such as edible films, hard gums, and digestion resistant starch which in the diet is correlated with fiber content.

Plant parts other than the grain of corn are also used in industry. Stalks and husks are made into paper and wallboard and cobs are used for fuel and to make charcoal.

The seed, the plant produced from the seed, and various parts of the plant can be utilized for human food, livestock feed, and as a raw material in industry.

DESCRIPTION OF THE INVENTION

This invention concerns starch containing actual amylose levels between about 76% and about 99%. The starch is produced from transgenic corn plants having a recombinant DNA sequence containing at least a portion of starch branching enzymes I and II.

A number of genes encoding carbohydrate branching enzymes have been isolated and sequenced. These include corn starch branching enzymes (Baba, T. et al. (1991) *Biochem. Biophys. Res. Commun.* 181:87-94; Fisher, D. K. et al. (1993) *Plant Physiol.* 102:1045-1046; Fisher, D. K. et al. (1995) *Plant Physiol.* 108:1313-1314). These genes can be isolated by techniques routinely employed by the skilled artisan for isolation of genes when the nucleotide sequence of the desired gene is known, as is the case for corn SBE genes (Kim, K. N. et al. (1998) *Gene* 216:233-243; Kim, K. N. et al. (1998) *Plant Mol. Biol.* 38:945-956), or when the sequence of a homologous gene from another organism is known. Sequence information about the desired gene can be used to prepare oligonucleotide probes for identification and isolation of the entire branching enzyme gene from an appropriate genetic library. This library may be a genomic library, wherein the coding region may be contained on a single DNA fragment or may be contained on several distinct DNA fragments. Moreover, two or more exons encoding the branching enzyme may be separated by one or more introns. Alternatively, the library may be a cDNA library wherein the likelihood of isolating a cDNA clone comprising the entire coding region as one contiguous sequence is greater. In either instance, the appropriate clone(s) can be identified by DNA-DNA hybridization with probes corresponding to one or more portions of the desired genes. Alternatively, oligonucleotide primers can be prepared and employed as PCR primers in order to amplify and subsequently isolate all or part of the branching enzyme coding region from genomic DNA, or from the genomic or cDNA libraries described above.

To have an effect on the fine structure of corn it is necessary for the transgene to be under the control of regulatory elements suitable for expression of the gene in the desired plant tissues. The regulatory elements should allow expression of the transgene at stages of development that provide the maximum desired effect and at levels of gene expression (where the result of expression of the transgene may be suppression of expression of an endogenous gene) that result in alteration of starch branching enzyme function.

The expression of foreign genes in plants, including corn, is well-established (Komari, T. et al. (1999) *Adv. Cell. Mol. Biol. Plants* 5:43-82; Klein, T. M. and Jones, T. J. (1999) *Adv. Cell. Mol. Biol. Plants* 5:21-42). Proper level of expression of sense branching enzyme genes in corn may require the use of different chimeric genes utilizing different regulatory elements. Moreover, effective modulation of endogenous branching enzyme gene expression by cosuppression may require construction of chimeric genes comprising different regions of the branching enzyme sense or antisense sequences. The well-known unpredictability of the cosuppression and antisense techniques indicates that even while using different genetic constructs, multiple plants may have to be screened in order to identify those with the desired phenotype.

Promoters utilized to drive gene expression in transgenic plants can be derived from many sources so long as the chosen promoter(s) have sufficient transcriptional activity to accomplish the invention by expressing RNA in the desired host tissue. Constitutive promoters are well described, for example Odell, J. et al. (1985) *Nature* 313:810-812. Preferred promoters for the present invention are those that allow expression specifically in seeds, since seeds are the primary location of long-term starch accumulation. In addition, seed-specific expression may avoid any potential deleterious effects that branching enzyme modulation may have on non-seed organs. Examples of seed-specific promoters include, but are not limited to, the promoters of seed storage proteins. The seed storage proteins are strictly regulated, being expressed almost exclusively in seeds in a highly organ-specific and stage-specific manner (Higgins et al. (1984) *Ann. Rev. Plant Physiol.* 35:191-221; Goldberg, R. B. et al. (1989) *Cell* 56:149-160; Thompson et al. (1989) *BioEssays* 10:108-113). Moreover, different seed storage proteins may be expressed at different stages of seed development. There are currently numerous examples for seed-specific expression of seed storage protein genes in transgenic plants. These include genes from monocotyledonous plants such as for barley β-hordein (Marris, C. et al. (1988) *Plant Mol. Biol.* 10:359-366) and wheat glutenin (Colot et al. (1987) *EMBO J* 6:3559-3564). Of particular use in the expression of the nucleic acid fragments of the invention are promoters from several extensively characterized corn seed storage protein genes such as endosperm-specific promoters of the 10 kD zein gene (Kirihara et al. (1988) *Gene* 71:359-

370), the 15 kD zein gene (Hoffman et al. (1987) *EMBO J.* 6:3213-3221; Schernthaner et al. (1988) *EMBO J.* 7:1249-1253; Williamson et al. (1988) *Plant Physiol.* 88:1002-1007), the 27 kD zein gene (Prat et al. (1987) *Gene* 52:51-49; Gallardo et al. (1988) *Plant Sci.* 54:211-281) and the 19 kD zein gene (Marks et al. (1985) *J. Biol. Chem.* 260:16451-16459). The relative transcriptional activities of these promoters in corn have been reported (Kodrzyck et al. (1989) *Plant Cell* 1:105-114) providing a basis for choosing a promoter for use in chimeric, gene constructs for corn. Moreover, promoters that drive the expression of genes encoding enzymes involved in starch biosynthesis may be used in the practice of this invention. These include the 5' regulatory sequences of the sucrose synthase (Yang, N.-S. and Russell, D. (1990) *Proc. Natl. Acad. Sci. USA* 87:4144-4148) and the waxy or granule-bound starch synthase I (Unger, E. et al. (1991) *Plant Physiol. Supp.* 96:124) genes. Promoter elements may be derived from other starch synthase (granule-bound and soluble isoforms) genes when these become available, and from the sh2 (Bhave et al. (1990) *Plant Cell* 2:581-588) and bt2 (Bae et al. (1990) *Maydica* 35:317-322) genes whose products constitute the enzyme ADP-glucose pyrophosphorylase. Genomic fragments encoding maize SBEI (Kim, K. N. et al. (1998) *Gene* 216:233-243) and SBEIIb (Kim, K. N. et al. (1998) *Plant Mol. Biol.* 38:945-956) have been isolated and DNA sequences required for SBE promoter activity have been identified (Kim, K. N. et al (1998) *Plant Mol. Biol.* 38:945-956; Kim, K. N. and Guiltinan, M. J. (1999) *Plant Physiol.* 121:225-236). The SBE promoter sequences can be used to ensure correct localization and timing of expression of transgenes built from intact or modified SBE coding regions or coding region fragments. While the expression level of promoters such as these is likely to be sufficient, one could envision using enhancers or enhancer-like elements (e.g. Odell, J. et al. (1988) *Plant Mol. Biol.* 10:263-272), including those found in introns (e.g. Callis et al. (1987) *Genes Dev.* 1:1183-1200), to further boost expression levels.

Any 3' non-coding region capable of providing a polyadenylation signal and other regulatory sequences that may be required for proper expression can be used to accomplish the invention. This would include the 3' end from any storage protein such as the 3' end of the 10 kd, 15 kd, 27 kd and alpha zein genes, the 3' end from viral genes such as the 3' end of the 35S or the 19S cauliflower mosaic virus transcripts, the 3' end from the opine synthesis genes, the 3' ends of ribulose 1,5-bisphosphate carboxylase or chlorophyll a/b binding protein, or 3' end sequences from any source such that the sequence employed provides the necessary regulatory information within its nucleic acid sequence to result in the proper expression of the promoter/coding region combination to which it is operably linked. There are numerous examples in the art that teach the usefulness of different 3' non-coding regions (for example, see Ingelbrecht, I. L. et al. (1989) *Plant Cell* 1:671-680).

Various methods of introducing a DNA sequence (i.e., of transforming) into eukaryotic cells of higher plants are available to those skilled in the art (see EPO publications 0 295 959 A2 and 0 138 341 A1). Such methods include high-velocity ballistic bombardment with metal particles coated with the nucleic acid constructs (see Klein, T. M. et al. (1987) *Nature* (London) 327:70-73, and U.S. Pat. No. 4,945,050), as well as those that utilize transformation vectors based on the Ti and Ri plasmids of *Agrobacterium* spp., particularly the binary type of these vectors. Ti-derived vectors transform a wide variety of higher plants, including corn (Ishida Y. et al. (1996) *Nature Biotech.* 14:745-750). One skilled in the art is familiar with still other means for the production of transgenic maize plants including introduction of DNA into protoplasts and regeneration of plants from said protoplasts (Omirulleh et al. (1993) *Plant Mol. Biol.* 21:415-423), electroporation of intact tissues (D'Hulluin et al. (1992) *Plant Cell* 4:1495-1505; Laursen et al. (1994) *Plant Mol. Biol.* 24:51-61), silica carbide mediated fiber transformation of maize cells (Kaeppler et al. (1992) *Theor. Appl. Genet* 84:560-566; Frame et al. (1994) *Plant J.* 6:941-948), among others. In addition to the method of particle bombardment of maize callus cells described above, one skilled in the art is familiar with particle bombardment of maize scutellar or suspension cultures to yield fertile transgenic plants (Koziel et al. (1993) *Bio/Technology* 11:194-200; Walters et al. (1992) *Plant Mol. Biol.* 18:189-200).

Once transgenic plants are obtained by one of the methods described above, it will be necessary to screen individual transgenics for those that most effectively display the desired phenotype. It is well known to those skilled in the art that individual transgenic plants carrying the same construct may differ in expression levels; this phenomenon is commonly referred to as "position effect". For example, when the construct in question is designed to express higher levels of the gene of interest, individual plants will vary in the amount of the protein produced and thus in enzyme activity; this in turn will effect the phenotype.

The person skilled in the art will know that special considerations are associated with the use of antisense or cosuppression technologies in order to reduce expression of particular genes. U.S. Pat. Nos. 5,190,931, 5,107,065 and 5,283,323 have taught the feasibility of these techniques, but it is well known that their efficiency is unpredictable. In either case, in order to save time, the person skilled in the art will make multiple genetic constructs containing one or more different parts of the gene to be suppressed, since the art does not teach a method to predict which will be most effective for a particular gene. Furthermore, even the most effective constructs will give an effective suppression phenotype only in a fraction of the individual transgenic lines isolated. For example, WO 93/11245 and WO 94/11516 teach that when attempting to suppress the expression of fatty acid desaturase genes in canola, actual suppression was obtained in less than 1% of the lines tested. In other species the percentage is somewhat higher, but in no case does suppression reach 100%.

This should not be seen as a limitation on the present invention, but instead as practical matter that is appreciated and recognized by the person skilled in this art. Accordingly, the skilled artisan will develop methods for screening large numbers of transformants. The nature of these screens will generally be chosen on practical grounds, and is not an inherent part of the invention. In the instant case, for example, one can screen by looking for changes in starch phenotype using chromatography to determine relative proportions of amylose to amylopectin, or amylopectin branch chain distribution. One could equally use antibodies specific for the branching enzyme encoded by the gene being suppressed, or one could establish assays that specifically measure branching enzyme activity. A preferred method will be one that allows large numbers of samples to be processed rapidly, since it will be expected that the majority of samples will be negative.

Plants that are identified to have the altered starch fine structure in the grain present unique genetic material which provide advantages over traditional corn lines and known starch mutants. Use of lines with inhibited expression of SBE isoforms in corn breeding provides a dominant trait that can simplify and speed the breeding process. Known starch mutants can be used but they are often recessive and present more complications. Further, the use of antisense or cosuppression to inhibit SBE isoforms leads to variable levels of inhibition due to chromosomal position effects. The resulting variable levels of SBE activities would lead to a wide range of phenotypes that is not possible using traditional mutants which can result in a limited dosage series of a mutant allele in corn endosperm.

The present invention can be used to generate transgenic plants whose starch is altered due to the suppression of starch branching enzymes to produce starches with industrial utility.

The disclosure of each reference set forth in this application is incorporated herein by reference in its entirety.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions. Thus, various modifications of the invention in addition to those shown and described herein will be apparent to those skilled in the art from the foregoing description. Such modifications are also intended to fall within the scope of the appended claims.

Example 1

Preparation of Recombinant Plasmids and Transgenic Plants

Recombinant Plasmids

The following example provides a description of DNA constructs that have been introduced into corn callus and used to produce suppression of starch branching enzyme gene expression in corn. The suppression causes decreased branching enzyme activity and results in changes in starch composition and fine structure elaborated below.

Separate constructs (pBE117 and pBE122) were designed for suppression of SBEI and SBEIIb expression. These constructs consist of:

i) a 1043 bp fragment of the 27 kD zein promoter directing expression of the transgene to corn endosperm;
ii) a modified SBEIIb or SBEI region;
iii) a 960 bp fragment of the 10 kD zein 3' end providing translational termination signals;
iv) in a modified pSP72 vector.

The modified pSP72 vector was prepared as follows. The commercially available pSP72 vector (Promega, Madison, Wis.) was modified to provide resistance to the antibiotic hygromycin by replacing the β-lactamase gene with a chimeric T7 promoter-hygromycin phosphotransferase-T7 terminator gene. An intermediary plasmid (pSPB38) was assembled with a 1.043 kb SalI-NcoI fragment of the promoter for the 27 kD zein gene directing the expression, in sense orientation, of a 636 bp fragment encoding a 10 kD high sulfur zein, and a 0.960 kb SmaI-PvuII fragment from the 3' end of the 10 kD zein gene. The modified pSP72 vector consists of plasmid pSPB38 having the 10 kD high sulfur zein coding region removed by digestion with NcoI and SmaI.

The modified SBEIIb region of plasmid pBE122 was assembled-using nucleotides 91-2117 of the published SBEIIb cDNA sequence (Fisher, D. K. et al. (1993) *Plant Physiol.* 102:1045-1046). A 347 bp deletion (encompassing nucleotides 1106-1452) was introduced into this segment of the SBEIIb sequence via combined HindIII and BsrGI digestion. The protruding ends were made blunt by treatment with mung bean nuclease and the plasmid recircularized by ligation. This rendered the DNA fragment incapable of producing active SBEIIb polypeptide. A 694 bp fragment from the 5' end of the SBEIIb cDNA sequence (nucleotides 91-784) was attached in antisense orientation to the 3' end of the sense SBEIIb segment to yield the modified SBEIIb fragment. This 2341 bp DNA fragment was cloned as an NcoI-SmaI fragment into the modified pSP72 vector prepared as explained above. The resultant plasmid is termed pBE122 and a diagram shown in FIG. 1.

Figure 2:
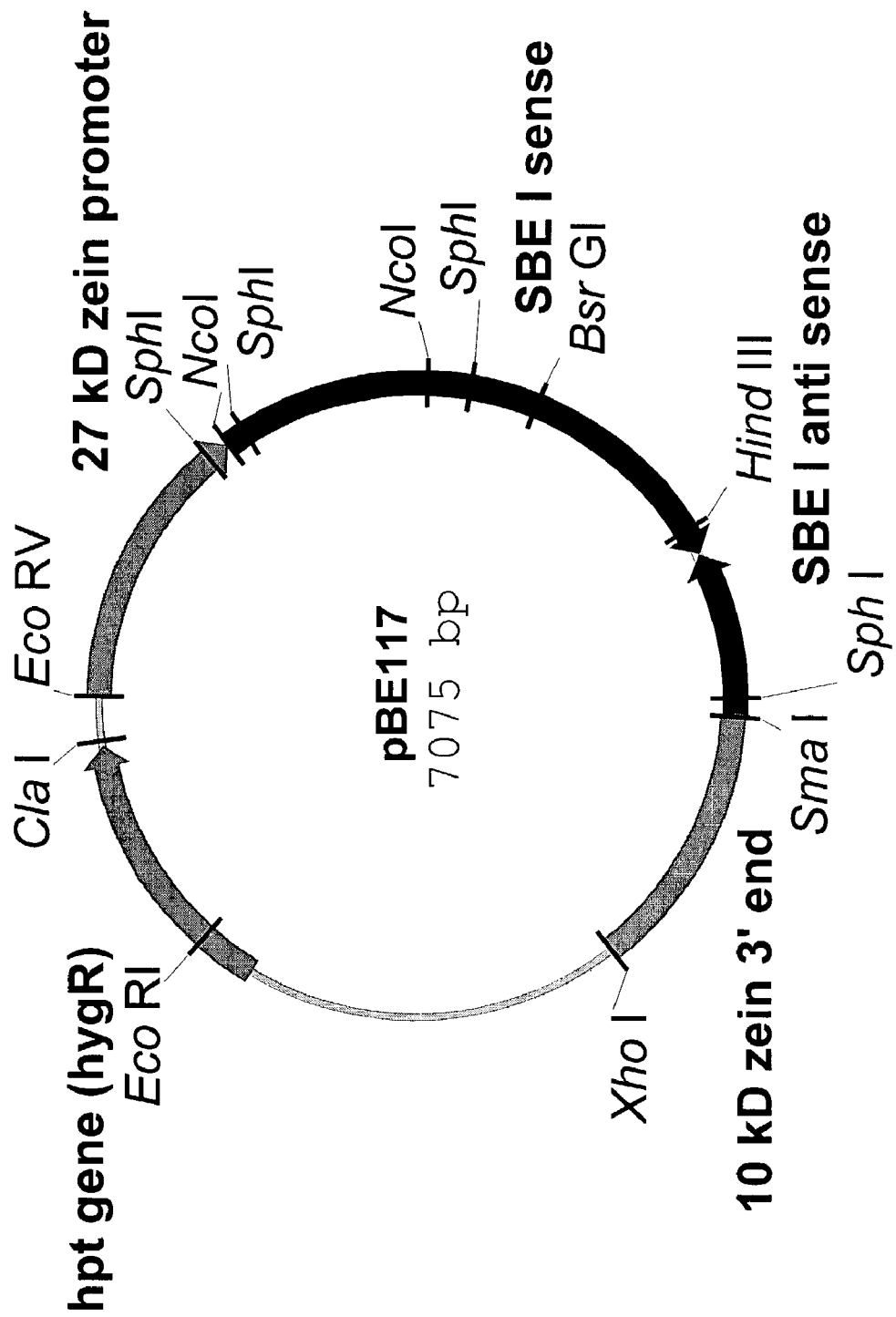

The modified SBEI region of pBE117 was assembled using a 2379 bp NcoI-HindIII fragment encompassing nucleotides 18 to 2390 of the published sequence (Fisher, D. K. et al. (1995) *Plant Physiol.* 108:1313-1314). An internal 523 bp deletion was created by digesting with BamHI and EcoRI, filling the overhangs using the Klenow fragment of DNA polymerase I and religating the blunt ends. A 708 bp XhoI-HindIII fragment consisting of nucleotides 18 through 698 was then ligated in antisense orientation to the 3' end of the deleted SBEI fragment. The modified SBEI region was cloned as a 2552 bp NcoI-SmaI fragment in the modified vector pSP72 to produce plasmid pBE117. A diagram of plasmid pBE117 is shown in FIG. 2.

Plant Transformation

Inbred corn lines LH132 and H99 were crossed. The resulting progeny were back-crossed to LH132 and a transformation line was developed by selecting for type II callus forming ability. Immature corn embryos were dissected from developing caryopses from the transformation line. Line LH132 is produced by Holden's Foundation Seed (Williamsburg, Iowa) and Line H99 is a public inbred line from Purdue University (West Lafayette, Ind.). The embryos were isolated 10 to 11 days after pollination when they were 1.0 to 1.5 mm long. The embryos were placed with the axis-side facing down and in contact with agarose-solidified N6 medium (Chu et al. (1975), *Sci. Sin. Peking* 18:659-668). The embryos were kept in the dark at 27° C. Friable embryogenic callus consisting of undifferentiated masses of cells with somatic proembryoids and embryoids borne on suspensor structures proliferated from the scutellum of these immature embryos. The embryogenic callus isolated from the primary explant was cultured on N6 medium and subcultured on this medium every 2 to 3 weeks.

Figure 3:
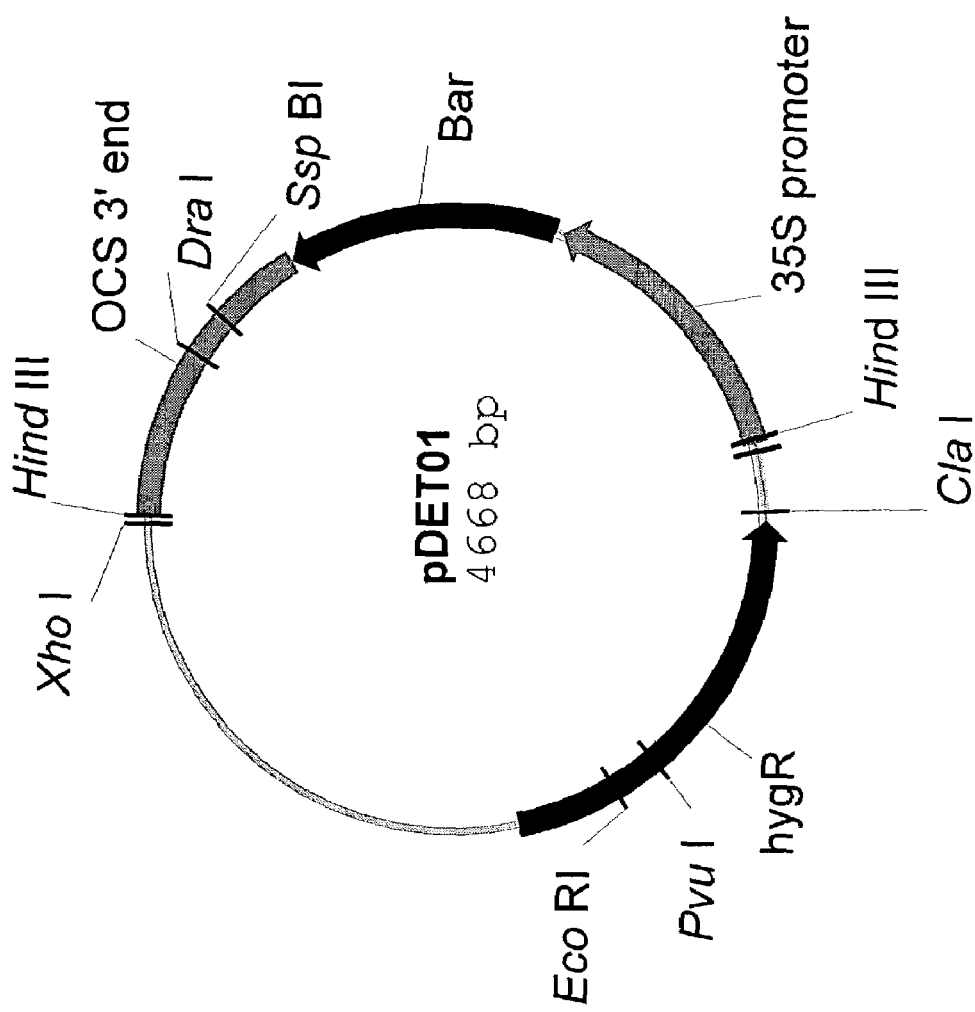
FIG. 3 shows a diagram of fragment pDET01. This DNA fragment contains sequences encoding the bar gene under the control of the Cauliflower Mosaic Virus 35S promoter and the 3' region of the OCS gene from *Agrobacterium tumefaciens*.

Particle bombardments were performed using isolated and purified DNA fragments. The recombinant DNA fragment containing the modified SBEI region was removed from plasmid pBE117 by digestion with EcoRV and XhoI. The recombinant DNA fragment containing the modified SBEII region was removed from plasmid pBE122 (FIG. 1) by digestion with EcoRV and DraI. The HindIII recombinant DNA fragment containing the bar gene under the control of the 35S promoter and containing the OCS region at the 3'-end was removed from plasmid pDET01. Plasmid pDET01 is shown in FIG. 3 and contains the bar gene (Murakami et al. (1986) *Mol. Gen. Genet.* 205:42-50; DeBlock et al. (1987) *EMBO J.* 6:2513-2518) which encodes phosphinothricin acetyl transferase (PAT). The enzyme PAT confers resistance to herbicidal glutamine synthetase inhibitors such as phosphinothricin (bialophos). The bar gene in pDET01 is under the control of the 35S promoter from Cauliflower Mosaic Virus (Odell, J. et al. (1985) Nature 313:810-812). The 3' region of the OCS gene from Agrobacterium tumefaciens is used as a transcription terminator.

The particle bombardment method (Klein, T. M. et al. (1987), Nature 327:70-73) was used to transfer genes to the callus culture cells. Gold particles (0.6 µm in diameter) were coated with DNA using the following technique. Fragments of DNA corresponding to the EcoRI/XhoI-digested pBE117 containing the modified SBEI regions (2 µg), the EcoRV/DraI-digested pBE122 containing the modified SBEII regions (2 µg), and the Hind III-digested pDET01 containing the Bar gene (1 µg) were added to 50 µL of a suspension of gold particles (60 mg per ml). Calcium chloride (50 µL of a 2.5 M solution) and spermidine free base (20 µL of a 0.1 M solution) were added to the particles. The suspension was vortexed during the addition of these solutions. The tubes were briefly centrifuged (5 sec at 15,000 rpm) and the supernatant removed. The particles were resuspended in 1 ml of absolute ethanol, centrifuged again and the supernatant removed. The ethanol rinse was performed again and the particles resuspended in a final volume of 50 µL ethanol. An aliquot (5 µL) of the DNA-coated gold particles was placed in the center of a Kapton® rupture disc (Bio-Rad Laboratories, Hercules, Calif.). The particles were accelerated into the corn tissue with a Biolistic™ PDS-1000/He (Bio-Rad Instruments, Hercules Calif.), using a helium pressure of 1100 psi, a gap distance of 0.5 cm and a flying distance of 1.0 cm.

For bombardment, the embryogenic tissue was placed on filter paper over agarose-solidified N6 medium. The tissue was arranged as a thin lawn and covered a circular area of about 5 cm in diameter. The petri dish containing the tissue was placed in the chamber of the PDS-1000/He approximately 8 cm from the stopping screen. The air in the chamber was then evacuated to a vacuum of 28 inches of Hg. The macrocarrier was accelerated with a helium shock wave using a rupture membrane that bursts when the He pressure in the shock tube reaches 1100 psi.

Four days after bombardment the tissue was transferred to N6 medium that contained bialaphos (5 mg per liter) and lacked casein. The tissue continued to grow slowly on this medium. After an additional 2 weeks the tissue was transferred to fresh N6 medium containing bialaphos. After 6 weeks, areas of about 1 cm in diameter of actively growing callus were identified on some of the plates containing the bialaphos-supplemented medium. These calli continued to grow when sub-cultured on the selective medium.

Callus samples were screened for the presence of the SBE transgenes by PCR analysis. DNA was extracted from approximately 100 µL of callus tissue by grinding in 500 µL extraction buffer (50 mM Tris-HCl, pH 8.0, 7 M urea, 0.35 M NaCl, 20 mM EDTA,1% n-lauryl sarkosine) in the presence of glass beads. Samples were extracted with a mixture of phenol-chloroform-isoamyl alcohol (25:24:1) and concentrated by precipitation with isopropanol. Each DNA was resuspended in 10 mM Tris-HCl, pH 8.0 and was used as the template in two separate PCR amplifications. In one reaction, primers 110A (SEQ ID NO:3) and 110B (SEQ ID NO:4) were used to screen for the presence of pBE117 DNA while in the second reaction, primers 95A (SEQ ID NO:5) and 95B (SEQ ID NO:6) were used to screen for the presence of pBE122.

```
                                           (SEQ ID NO:3)
110A:    5'-CAC GCG ATG GCA TGT CAA CTC A-3'

(SEQ ID NO:4)
110B:    5'-CCT TTC TCC GCC CCG CAC CTG T-3'

(SEQ ID NO:5)
95A:     5'-TGG CCC TCG ATA GAC CTT CAA CTC C-3'

(SEQ ID NO:6)
95B:     5'-CAC GCG ATG GCA TGT CAA CTC A-3'
```

For amplification, 1 µL DNA was combined with 20 µM of each of the appropriate primers in a 25 µL reaction mixture specified by REDTaq™ ReadyMix™ PCR Reaction Mix (Sigma). Amplification was carried out for 40 cycles consisting of 30 seconds at 95° C., 1 minute at 60° C., and 1 minute at 72° C., followed by a 5 minute extension at 72° C. Samples were scored for the presence of SBEI or SBEIIb as follows. An 867 bp band indicated the presence of SBEI. This band corresponds to the 3' portion of the SBEI segment and the 10 kD zein 3' end in pBE117. A 1070 bp band indicated the presence of SBEIIb. This band corresponds to the 3' portion of the SBEIIb segment and the 10 kD zein 3' end in pBE122.

Callus samples that tested positive for the presence of both SBE transgenes were carried forward in the regeneration regimen. Plants were regenerated from the transgenic callus by first transferring clusters of tissue to N6 medium supplemented with 0.2 mg per liter of 2,4-dichlorophenoxy-acetic acid (2,4-D) (Invitrogen Life Technologies, Carlsbad, Calif.) in order to increase the amount of tissue sample. After two weeks, the tissue was transferred to regeneration medium (Fromm et al. (1990) Bio/Technology 8:833-839). A total of 119 transgenic events were regenerated from two experiments separately yielding 37 and 82 PCR positive events.

Example 2

Starch Extraction and Analysis

Starch was isolated from seeds obtained from ATCC having Accession No. 75182, and from seeds obtained from the above-prepared transgenic plants. Specifically, the samples shown in Table 1 were derived from three independent transgenic events (indicated as XBG08223, XBG08085, and XBG08227) at the R1 generation (the seeds on the primary transformant) and in one case, XAY25432, from the R2 generation of one of the same events (XBG08227). Hylon® VII starch was obtained from National Starch and Chemical Company, Bridgewater, N.J. The isolated starches were enzymatically debranched and submitted to Gel Permeation Chromatography (GPC) to determine the amylose and amylopectin content of the seeds.

Starch Extraction

Individual seeds were placed into wells of a 5 ml 48-well microplate (hereon referred to as sample microplate) and 3 ml of steep solution (1.2% v/v lactic acid, 0.3% w/v sodium metabisulfite, pH 3.8) was added. The sample microplate was covered with two stacked supersoft neoprene rubber gaskets (⅛ inch thick each) and sealed using a standard clamp. A standard clamp is comprised of aluminum bottom and top plates (6 inches by 4.375 inches by 0.25 inches). The bottom plate has four guide rods (⅜ inch diameter, 1.75 inch length) and four attached toggle clamps, and the top plate has four ⅜ inch diameter holes and four toggle clamp hooks. The assembled unit was placed in a 52° C. oven and shaken for 24 hours for the corn to steep. After 24 hours the microplate assembly was removed from the oven, the clamp disassembled, and the gaskets removed. A 6-mesh sieve was held securely over the sample microplate, the unit inverted, and the liquid poured off. The samples were rinsed with water and similarly drained.

The seeds were coarsely mashed using a 48-prong masher. Five frozen 440 stainless steel balls (¼-inch diameter) and 3 ml of refrigerated deionized water were added to each well. The sample microplate was covered with a microplate lid and the assembly placed in a −80° C. freezer for five minutes.

The sample microplate was covered with two supersoft neoprene rubber gaskets (⅛ inch thick each) and sealed using a shaking clamp. A shaking clamp is a standard clamp with the bottom plate extended to 8.875 inches (to position the center of the microplate 8.25 inches from the center of the shaker arm). This bottom plate also has two ⅜-inch diameter securing holes. The seeds were homogenized using a modified Red Devil model 5400 paint shaker (Erichsen, Hemer, Germany). The modified paint shaker contains balsa wood inserts attached to the paint can clamps and these inserts have two ⅜-inch diameter securing pins. The securing holes in the shaking clamps were aligned with the securing pins and clamp tightened in place. After shaking the samples for 180 seconds, the shaking clamp was removed from the paint shaker. The sample microplate was removed from the shaking clamp and the top wiped off with a towel.

A 48-hole microplate lid (¼ inch×9/16 inch holes) was pressed on to the sample microplate and a 48-hole supersoft neoprene gasket (¼ inch×9/16-inch holes, 1/16 inch thick) was added on top. The microplate assembly was put in the bottom of a filter clamp. A filter clamp is a modified standard clamp having guide-rods that are 3.875 inches long. A fresh 48-well microplate (from hereon referred to as collection microplate) was placed inverted over the sample microplate and the unit carefully clamped together. After turning over and shaking by hand several times, the clamped unit was kept in the inverted position and the microplate assembly removed. The sample microplate, which retains the steel balls due to the 48-hole microplate lid, was quickly removed and the top of the collection microplate was wiped clean with a fresh towel.

The collection microplate was centrifuged at 2500 rpm for 1.5 minutes using an IEC Centra® MP4 centrifuge with microplate carousels (Needleham Heights, Mass.). The supernatant was decanted and discarded and a single 440 stainless steel ball (¼ inch diameter) and 1 ml deionized water were added to each well. A filter lid was pressed onto the collection microplate and covered with the 48-hole neoprene gasket. A filter lid is a 48-hole microplate lid which has 75 µm stainless steel mesh melded over each opening. The sample microplate was inverted over the collection microplate and the assembly placed in the filter clamp. The clamped assembly was then inverted, secured in a custom-made vertical shaker (3.5 inches of vertical travel), and shaken at 140 revolutions per minute until all the fluid was filtered into the sample microplate. The sample microplate was removed, centrifuged, and decanted as before.

One borosilicate glass bead (¼-inch diameter) and 1.9 ml each of 100 mM sodium chloride and toluene were added to each well of the sample microplate. The sample microplate was covered with a Viton® gasket (1/16 inch thick) and two supersoft neoprene gaskets (⅛ inch thick each), placed in a standard clamp, and shaken in the modified paint shaker. After shaking for 10 seconds, the sample microplate was removed and centrifuged for 15 seconds at a setting of 1700 rpm. The organic layer was aspirated off and 1.9 ml of toluene and 1 ml of 100 mM sodium chloride were added to each well of the sample microplate. The sample microplate was covered, clamped, shaken, centrifuged for 11 seconds at a setting of 1500 rpm, and the organic layer aspirated off. The samples were washed two more times with toluene and sodium chloride but this time the organic layer was removed after separating by settling for 30 minutes. Deionized water (2.6 ml) was added to each well after removing the last toluene aliquot. The sample microplate was covered with the Viton® and neoprene gaskets, secured with a standard clamp, and shaken by hand for 10 seconds. The microplate was then removed, centrifuged for 1.5 minutes at 3000 rpm, and all water aspirated. The samples were washed two more times, once with 3 ml of deionized water and once with 3 ml of acetone, and the starch dried overnight in a 45° C. oven.

Enzymatic Debranching of Starch

The sample microplate, containing the dried starch, was covered with a microplate lid having a 1/16 inch thick neoprene gasket attached (hereon referred to as weigh lid). The unit was secured in a shaking clamp, placed in the modified paint shaker, and shaken for 45 seconds. The shaking clamp was removed and disassembled. The weigh lid, having starch attached in the imprint of each well, was carefully removed and placed over a new 48-well microplate containing 1 ml deionized water in each well. This unit was then clamped with the shaking clamp and shaken several times by hand to disperse the starch into the water.

The weigh lid was removed and the top of the microplate wiped with a towel. The microplate, containing the dispersed starch in water, was covered with a 1/16-inch thick high-temperature silicone gasket and a ⅛-inch thick supersoft neoprene gasket, and placed in a cook clamp. A cook clamp is a standard clamp having shortened toggle screws to create a tighter seal. This assembly was shaken side-to-side by hand and placed in a 125° C. oven. The samples were heated for 1 hour, shaking every 15 minutes, to ensure starch dispersal. The entire assembly was removed from the oven, cooled under running water, and then placed in a room-temperature water bath for 10 minutes. The microplate was uncovered and the temperature was monitored from an internal well. Once the temperature reached 45° C., 50 µl of isoamylase solution [1 µl Megazyme isoamylase (Promega, Madison, Wis.) in 49 µl 50 mM sodium acetate, pH 4.5] were added to each well. The microplate was assembled in the same manner, clamped in the cook clamp, and placed in a 45° C. water bath for 3.5 hours, shaking once every hour.

The microplate was removed from the assembly and the contents from each well were transferred to a 2 ml 96-well microplate. The 96-well microplate was covered with Miracloth, secured with rubber bands, and frozen at −80° C. for 1.5 hours. The samples were lyophilized for 40 hours using a Labconco freeze-dry system. The Miracloth was removed and 500 µl DMSO were added to each well. The 96-well microplate was covered with two supersoft neoprene gaskets (⅛ inch thick each) and placed in a standard clamp. The assembly was shaken by hand initially and every 15 minutes for 1.5 hours. The 96-well microplate was removed and the top wiped with a towel.

Amylose and Amylopectin Determination

Aliquots (250 µl) were removed from each well, transferred to clean 300 µl chromatography vials, and capped. The vials were heated in a 55° C. oven for 30 minutes. One hundred µl of each sample was injected into a Waters 2690 Separations Module (Milford, Mass.) having a series of four Polymer Laboratories (Amherst, Mass.) organic GPC columns. These columns were one 50×7.5 mm PLgel 5 µm MiniMIX-C and three 300×7.5 mm PLgel 5 µm MiniMIX-Cs. The column heater temperature was set at 100° C. and the flow rate of HPLC-grade DMSO was set at 0.65 ml/min. A Viscotek (Houston, Tex.) T60A dual detector (in-line viscometry and right-angle laser light scattering) and a Waters 410 refractometer at 50° C. were connected in series and used to measure the molecular size, molecular weight, and concentration of the post-column material. Data was analyzed using Viscotek's TriSec® software. Typical gel permeation chromatograms are shown in FIGS. 4 through 7.

Figure 4:
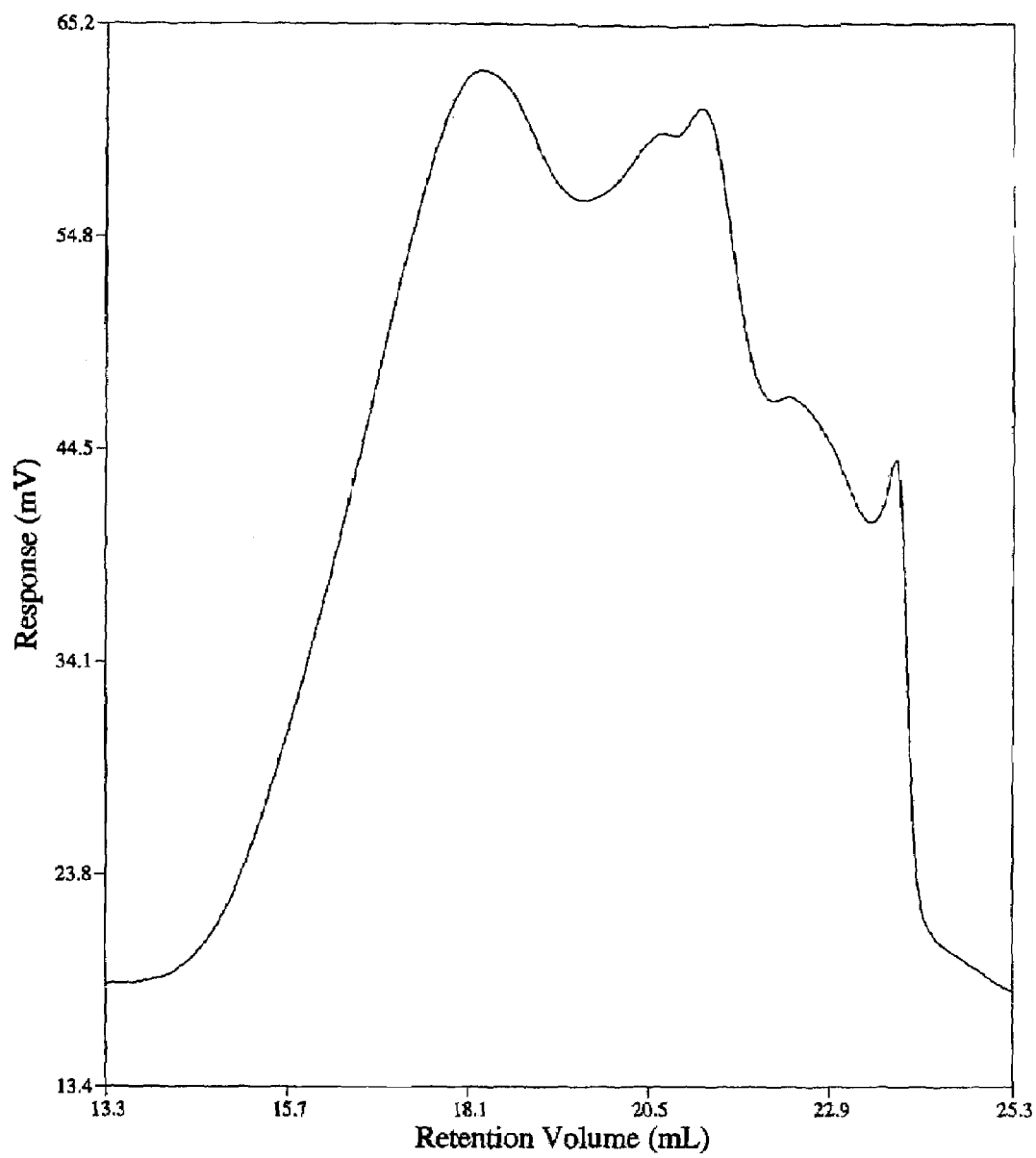
FIG. 4 shows a typical gel permeation chromatogram obtained from debranched starch derived from seed having ATCC Accession No. 75182.
Figure 5:
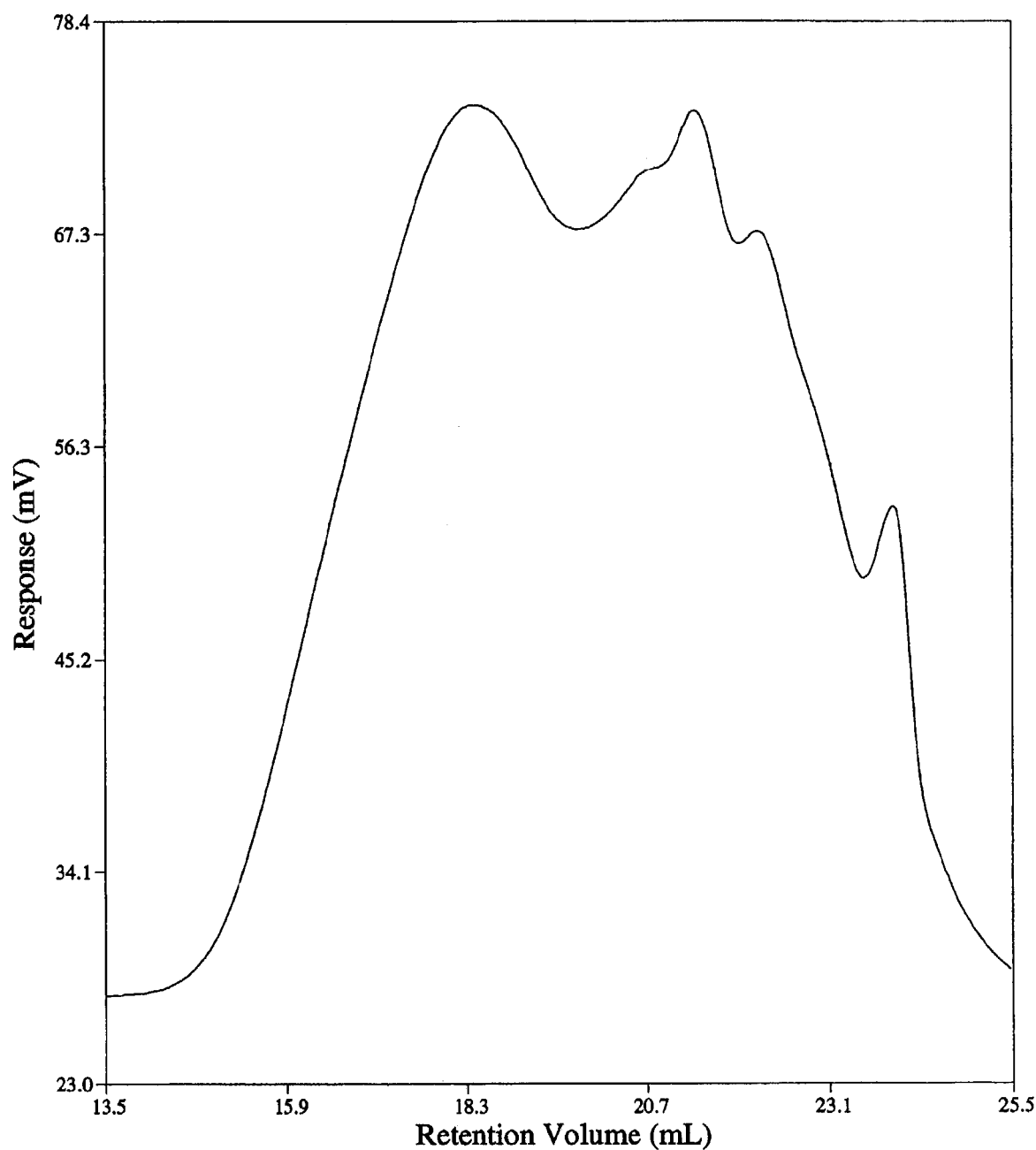
FIG. 5 shows a typical gel permeation chromatogram obtained from Hylon® VII debranched starch.
Figure 6:
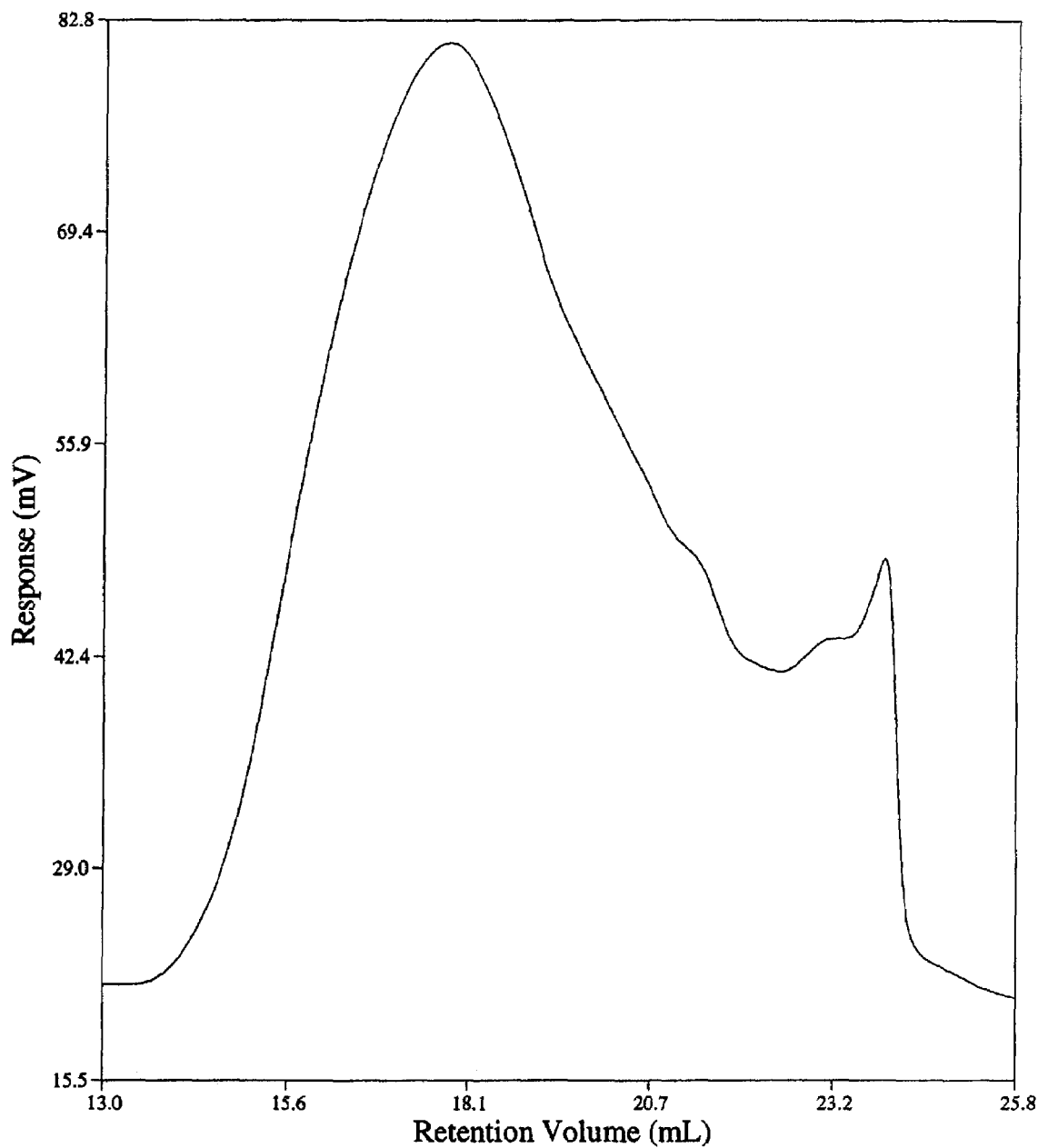
FIG. 6 shows a typical gel permeation chromatogram obtained from debranched starch derived from the R1 seeds labeled XBG08227 of the present invention.
Figure 7:
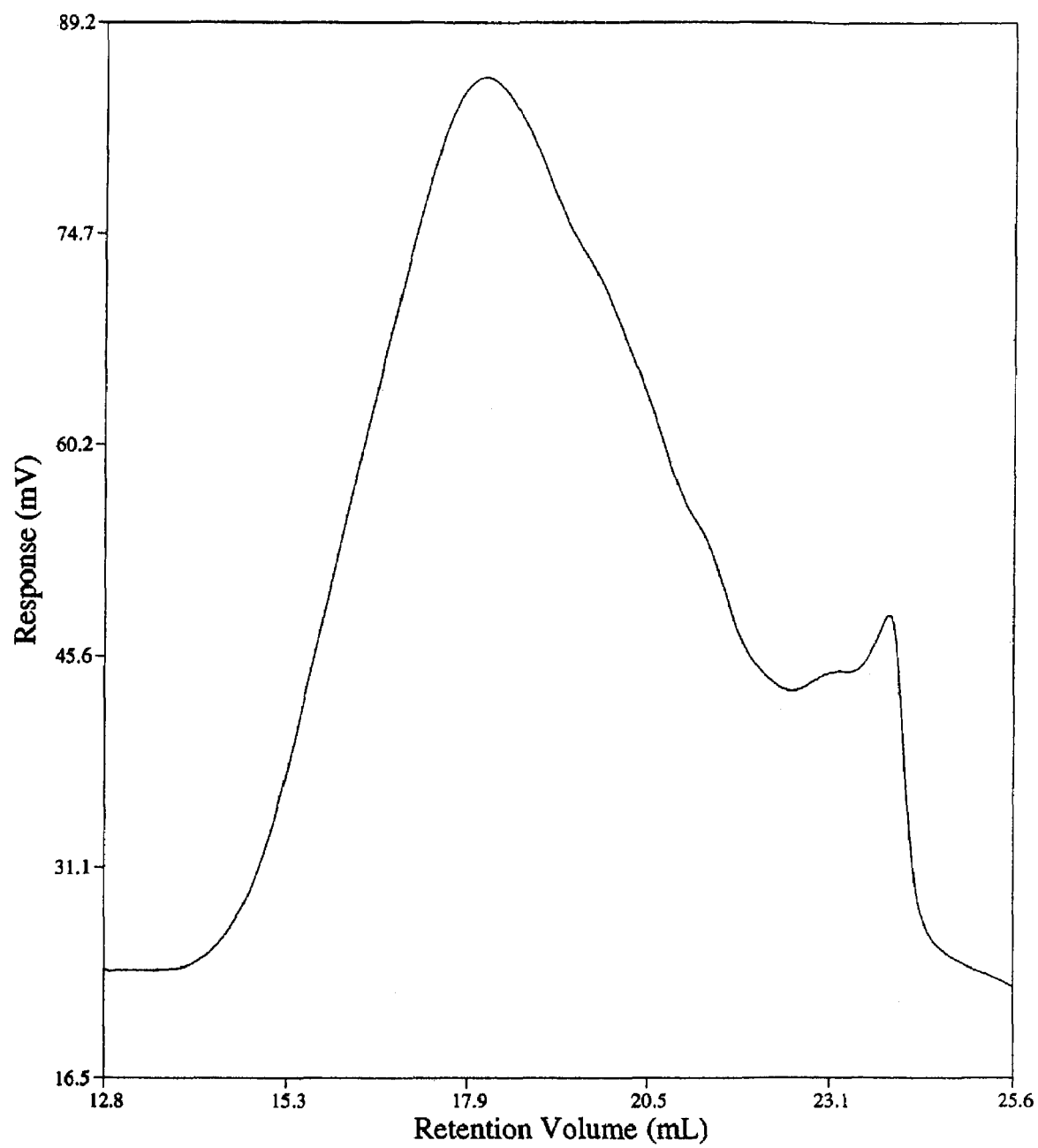
FIG. 7 shows a typical gel permeation chromatogram obtained from debranched starch derived from the R2 seeds labeled XAY24432 of the present invention.

The results obtained from the GPC chromatography of enzymatically debranched gelatinized starches are shown below. A GPC chromatogram obtained from debranched starch derived from seeds bearing ATCC Accession No. 75182 is shown in FIG. 4; a GPC chromatogram obtained from Hylon® VII debranched starch is shown in FIG. 5; a GPC chromatogram obtained from debranched starch derived from the R1 seeds labeled XBG08227 is shown in FIG. 6; and a GPC chromatogram obtained from debranched starch derived from the R2 seeds labeled XAY24432 is shown in FIG. 7. Table 1 displays the number of seeds analyzed, the amylose and amylopectin areas (in mm), and the percent of actual amylose determined for the different samples.

The results obtained from the GPC chromatography of enzymatically debranched gelatinized starches are shown below. Table 1 displays the results of single seed analysis, including the number of the individual seed of the cob analyzed, the amylose and amylopectin areas (in square mm), and the percent of actual amylose determined for the different samples. In most cases only one single seed per cob is shown. For two cobs, data from two individual seeds are presented and produced, as would be expected, very similar results. In the case of the highest actual amylose level, seeds from the next generation were analyzed (XAY25432), and the data show that the trait is stably inherited.

TABLE 1

Analysis of Actual Amylose Content of Different Corn Starches

| Sample | Seed Number | Amylose Area | Amylopectin Area | % Actual Amylose |
|---|---|---|---|---|
| Hylon ® VII | na* | 160 | 144 | 53 |
| XBG08223 | 4 | 239 | 76 | 76 |
| XBG08223 | 5 | 249 | 70 | 78 |
| XBG08085 | 4 | 256 | 59 | 81 |
| XBG08085 | 5 | 262 | 55 | 83 |
| XAY25432 | 4 | 297 | 19 | 94 |
| XBG08227 | 3 | 299 | 22 | 93 |
| ATCC75182 | 2 | 141 | 129 | 52 |

*The Hylon ® VII starch was obtained commercially and processed with the other samples.

When the above data is combined with literature values for potentiometric iodine determination where possible, a comparison as shown in Table 2 can be made.

TABLE 2

Amylose Content of Maize Starches Measured by Different Methods

| | Amylose Measurement Method | |
|---|---|---|
| | Potentiometric Iodine | Debranching/GPC |
| Dent | 27.0[1] | 26.7[2] |
| Hylon ® VII | 71.0[1] | 53.0[2] |
| LAPS | 89.9[1] | 52.9[5] |
| ATCC75182 | 85.0[3] | 52.0[4] |

[1]As indicated in Shi et al., (1998) J. Cereal Sci. 27: 289–299 (hereinafter "Shi et al.") see Table II.
[2]As determined in accordance with the present invention.
[3]U.S. Pat. No. 5,977,454
[4]The highest value obtained for ATCC75182 by debranching/GPC, as shown in Table 1 above.
[5]As indicated in Shi et al., Table IV.

The material referred to as "LAPS" by Shi et al. is a maize starch, not publicly available. The value of 52.9 is from Shi et al., Table IV. In Shi et al., Table V, the same material is referred to as having 79.9% amylose by GPC. This confusion arises from the inclusion of "low molecular weight amylose" in the 79.9% amylose result. Table IV, however, includes low molecular weight amylose in column F2, and thus the value for LAPS in Table IV is 52.9%. Low molecular weight amylose has a degree of polymerization of only 92-95 (Shi et al., pg. 292), and thus is not amylose. As indicated throughout the subject application, amylose has a degree of polymerization of up to several thousand. In a later manuscript on potato starch written by in part the same authors (Schwall et al. (2000) Nature Biotech. 18:551-554), maize LAPS is referred to as having 53% amylose as determined by GPC (page 553, 2nd column). This value is consistent with Shi et al., Table IV that discloses 52.9% amylose by GPC.

U.S. Pat. No. 5,300,145 (the '145 patent) discloses low amylopectin starch as having more amylose than the starch from Hylon® VII. In the '145 patent, the average amylose content of the low amylopectin starch and the Hylon VII starch were measured using potentiometric and colorimetric methods, see '145 patent, column 13, Table IIA. The average amylose content obtained by potentiometric method was 70.8 for Hylon® VII and 86.9% for the low amylopectin starch; the average amylose content obtained using colorimetric methods was 72.2% for Hylon® VII and 83.6% for the low amylopectin starch. Thus, when compared to Hylon® VII starch, the low amylopectin starch has no more than 16.1% additional amylose. When using the debranching and GPC method, Hylon VII starch has 53.0% amylose, we assume that the low amylopectin starch has no more than 70% amylose.

In conclusion, it is clear from the data presented here that amylose levels in the literature must be examined with care, taking into account the methods used. Combining the data shown in Example 2, the actual amylose levels of the starch of the present invention are significantly higher than those of starches previously reported as being high in amylose.

What is claimed is:

1. An isolated corn starch comprising at least about 76% actual amylose.

2. The starch of claim 1 wherein said starch comprises about 80% actual amylose.

3. The starch of claim 1 wherein said starch comprises about 85% actual amylose.

4. The starch of claim 1 wherein said starch comprises about 90% actual amylose.

5. The starch of claim 1 wherein said starch comprises about 95% actual amylose.

6. A corn starch extracted from a corn plant source, said starch comprising at least about 76% actual amylose, said corn plant source comprising at least one recombinant DNA molecule comprising at least a portion of corn starch branching enzymes I and II, wherein said at least one recombinant DNA molecule is sufficient to suppress the endogenous expression of corn starch branching enzymes I and II, or any progeny thereof, wherein said progeny comprise said at least one recombinant DNA molecule.

7. The corn starch of claim 6 wherein said recombinant DNA molecule comprises a first molecule comprising at least a portion of starch branching enzyme I and a second molecule comprising at least a portion of starch branching enzyme II.

8. A corn starch of claim 6 wherein said corn plant source comprises one recombinant DNA molecule comprising at least a portion of starch branching enzyme I and at least a portion of starch branching enzyme II.

9. The starch of claim 6 wherein said starch comprises about 80% actual amylose.

10. The starch of claim 6 wherein said starch comprises about 85% actual amylose.

11. The starch of claim 6 wherein said starch comprises about 90% actual amylose.

12. The starch of claim 6 wherein said starch comprises about 95% actual amylose.

13. The corn starch of claim 1 wherein said corn plant source is a kernel.

14. The corn starch of claim 6 wherein said corn plant source is a kernel.

15. An isolated corn starch comprising at least about 76% relative amylose as determined by gel permeation chromatography after enzymatic debranching of the starch.

16. The isolated corn starch of claim 15 wherein said isolated corn starch comprises from about 80% to about 95% relative amylose as determined by gel permeation chromatography after enzymatic debranching of the starch.

17. The isolated corn starch of claim 15 wherein said isolated corn starch comprises from about 85% to about 90% relative amylose as determined by gel permeation chromatography after enzymatic debranching of the starch.

18. The isolated corn starch of claim 15 wherein said isolated corn starch is a corn starch extracted from a corn plant source comprising one recombinant DNA molecule comprising at least a portion of starch branching enzyme I and at least a portion of starch branching enzyme II.

* * * * *

SEQUENCE LISTING

<160> NUMBER OF SEQ ID NOS: 6

<210> SEQ ID NO 1

-continued

```
<211> LENGTH: 2443
<212> TYPE: DNA
<213> ORGANISM: Artificial Sequence
<220> FEATURE:
<221> NAME/KEY: misc_feature
<222> LOCATION: (1)..(2443)
<223> OTHER INFORMATION: SBEII modified region

<400> SEQUENCE: 1
catggatggc gttccgggtt tctgggcgg  tgctcggtgg ggccgtaagg gctccccgac      60
tcaccggcgg cggggagggt agtctagtct tccggcacac cggcctcttc ttaactcggg     120
gtgctcgagt tggatgttcg gggacgcacg gggccatgcg cgcggcggcc gcggccagga     180
aggcggtcat ggttcctgag ggcgagaatg atggcctcgc atcaagggct gactcggctc     240
aattccagtc ggatgaactg gaggtaccag acatttctga agagacaacg tgcggtgctg     300
gtgtggctga tgctcaagcc ttgaacagag ttcgagtggt ccccccacca agcgatggac     360
aaaaaatatt ccagattgac cccatgttgc aaggctataa gtaccatctt gagtatcggt     420
acagcctcta tagaagaatc cgttcagaca ttgatgaaca tgaaggaggc ttggaagcct     480
tctcccgtag ttatgagaag tttggattta atgccagcgc ggaaggtatc acatatcgag     540
aatgggctcc tggagcattt tctgcagcat tggtgggtga cgtcaacaac tgggatccaa     600
atgcagatcg tatgagcaaa aatgagtttg tgtttgggaa atttttctg  cctaacaatg     660 cagatggtac atcacctatt cctcatggat ctcgtgtaaa ggtgagaatg gatactccat     720
caggataaaa ggattcaatt ccagcctgga tcaagtactc agtgcaggcc ccaggagaaa     780
taccatatga tgggatttat tatgatcctc ctgaagaggt aaagtatgtg ttcaggcatg     840
cgcaacctaa acgaccaaaa tcattgcgga tatatgaaac acatgtcgga atgagtagcc     900
cggaaccgaa gataaacaca tatgtaaact ttagggatga agtcctccca agaataaaaa     960
aacttggata caatgcagtg caaataatgg caatccaaga gcactcatat tatgaactc    1020 accacggatt acaagtaaca tttacgggga acttcaatga gtattttggc tttgccaccg    1080
atgtagatgc agtggtttac ttgatgctgg taaatgatct aattcatgga ctttatcctg    1140
aggctgtaac cattggtgaa gatgttagtg gaatgcctac atttgcccct cctgttcacg    1200
atggtggggt aggttttgac tatcggatgc atatggctgt ggctgacaaa tggattgacc    1260
ttctcaagca aagtgatgaa acttggaaga tgggtgatat tgtgcacaca ctgacaaata    1320
ggaggtggtt agagaagtgt gtaacttatg ctgaaagtca tgatcaagca ttagtcggcg    1380
acaagactat tgcgttttgg ttgatggaca aggatatgta tgatttcatg gccctcgata    1440
gaccttcaac tcctaccatt gatcgtggga tagcattaca taagatgatt agacttatca    1500
caatgggttt aggaggagag ggctatctta atttcatggg aaatgagttt ggacatcctg    1560
aatggataga tttccaaga  ggtccgcaaa gacttccaag tggtaagttt attccaggga    1620
ataacaacag ttatgacaaa tgtcgtcgaa gatttgacct gggtgatgca gactatctta    1680
ggtatcatgg tatgcaagag tttgatcagg caatgcaaca tcttgagcaa aaatatgaat    1740
tcttacacga gatccatgag gaataggtga tgtaccatct gcattgttag gcagaaaaat    1800
ttcccaaaca ccaaactcat ttttgctcat acgatctgca tttggatccc agttgttgac    1860
gtcacccacc aatgctgcag aaaatgctcc aggagcccat tctcgatatg tgataccttc    1920
cgcgctggca ttaaatccaa acttctcata actacgggag aaggcttcca agcctccttc    1980
atgttcatca atgtctgaac ggattcttct atagaggctg taccgatact caagatggta    2040
cttatagcct tgcaacatgg ggtcaatctg gaatatttt  tgtccatcgc ttggtggggg    2100
```

```
gaccactcga actctgttca aggcttgagc atcagccaca ccagcaccgc acgttgtctc    2160
ttcagaaatg tctggtacct ccagttcatc cgactggaat tgagccgagt cagcccttga    2220
tgcgaggcca tcattctcgc cctcaggaac catgaccgcc ttcctggccg cggccgccgc    2280
gcgcatggcc ccgtgcgtcc ccgaacatcc aactcgagca ccccgagtta agaagaggcc    2340
ggtgtgccgg aagactagac taccctcccc gccgccggtg agtcggggag cccttacggc    2400
cccaccgagc accgcccag aaacccggaa cgccatccat ccc                       2443
```

<210> SEQ ID NO 2
<211> LENGTH: 2551
<212> TYPE: DNA
<213> ORGANISM: Artificial Sequence
<220> FEATURE:
<221> NAME/KEY: misc_feature
<222> LOCATION: (1)..(2551)
<223> OTHER INFORMATION: SBEI modified region

<400> SEQUENCE: 2

```
catggtgtgc ctcgtgtcgc cctcttcctc gccgactccg cttccgccgc cgcggcgctc    60
tcgctcgcat gctgatcggg cggcaccgcc ggggatcgcg ggtggcggca atgtgcgcct    120
gagtgtgttg tctgtccagt gcaaggctcg ccggtcaggg gtgcggaagg tcaagagcaa    180
attcgccact gcagctactg tgcaagaaga taaaactatg caactgcca aaggcgatgt     240 cgaccatctc cccatatacg acctggaccc caagctggag atattcaagg accatttcag    300
gtaccggatg aaaagattcc tagagcagaa aggatcaatt gaagaaatg agggaagtct     360 tgaatctttt tctaaaggct atttgaaatt tgggattaat acaaatgagg atggaactgt    420
atatcgtgaa tgggcacctg ctgcgcagga ggcagagctt attggtgact tcaatgactg    480
gaatggtgca aaccataaga tggagaagga taaatttggt gtttggtcga tcaaaattga    540
ccatgtcaaa gggaaacctg ccatccctca caattccaag gttaaatttc gctttctaca    600
tggtggagta tgggttgatc gtattccagc attgattcgt tatgcgactg ttgatgcctc    660
taaatttgga gctccctatg atggtgttca ttgggatcaa ttcatgtttg atggcttccg    720
atttgatgga gttacatcaa tgctgtatca tcaccatggt atcaatgtgg ggtttactgg    780
aaactaccag gaatatttca gtttggacac agctgtggat gcagttgttt acatgatgct    840
tgcaaaccat ttaatgcaca aactcttgcc agaagcaact gttgttgctg aagatgtttc    900
aggcatgccg gtccttttgcc ggccagttga tgaaggtggg gttgggtttg actatcgcct    960
ggcaatggct atccctgata gatggattga ctacctgaag aataaagatg actctgagtg    1020
gtcgatgggt gaaatagcgc atactttgac taacaggaga tatactgaaa aatgcatcgc    1080
atatgctgag agccatgatc agtctattgt tggcgacaaa actattgcat ttctcctgat    1140
ggacaaggaa atgtacactg gcatgtcaga cttgcagcct gcttcaccta caattgatcg    1200
agggattgca ctccaaaaga tgattcactt catcacaatg gcccttggag gtgatggcta    1260
cttgaatttt atgggaaatg agtttggtca cccagaatgg attgactttc caagagaagg    1320
gaacaactgg agctatgata aatgcagacg acagtggagc cttgtggaca ctgatcactt    1380
gcggtacaag tacatgaatg cgtttgacca agcgatgaat gcgctcgatg agagattttc    1440
cttcctttcg tcgtcaaagc agatcgtcag cgacatgaac gatgaggaaa aggttattgt    1500
ctttgaacgt ggagattag ttttttgtttt caatttccat cccaagaaaa cttacgaggg     1560
ctacaaagtg ggatgcgatt tgcctgggaa atacagagta gccctggact ctgatgctct    1620
```

-continued

```
ggtcttcggt ggacatggaa gagttggcca cgacgtggat cacttcacgt cgcctgaagg    1680
ggtgccaggg gtgcccgaaa cgaacttcaa caaccggccg aactcgttca aagtcctttc    1740
tccgccccgc acctgtgtgg cttattaccg tgtagacgaa gcaggggctg acgacgtct     1800 tcacgcgaaa cgagagacag gaaagacgtc tccagcagag agcatcgacg tcaaagcttg    1860
caccatcata gggagctcca aatttagagg catcaacagt cgcataacga atcaatgctg    1920
gaatacgatc aacccatact ccaccatgct atagaaagcg aaatttaacc ttggaattgt    1980
gagggatggc aggtttccct ttgacatggt caattttgat cgaccaaaca ccaaatttat    2040
ccttctccat cttatggttt gcaccattcc agtcattgaa gtcaccaata agctctgcct    2100
cctgcgcagc aggtgcccat tcacgatata cagttccatc ctcatttgta ttaatcccaa    2160
atttcaaata gcctttagaa aaagattcaa gacttccctc attttcttca attgatcctt    2220
tctgctctag gaatcttttc atccggtacc tgaaatggtc cttgaatatc tccagcttgg    2280
ggtccaggtc gtatatgggg agatggtcga catcgccttt ggcagttgcc atagttttat    2340
cttcttgcac agtagctgca gtggcgaatt tgctcttgac cttccgcacc cctgaccggc    2400
gagccttgca ctggacagac aacacactca ggcgcacatt gccgccaccc gcgatccccg    2460
gcggtgccgc ccgatcagca tgcgagcgag agcgccgcgg cggcggaagc ggagtcggcg    2520
aggaagaggg cgacacgagg cacaccatcc c                                   2551
```

```
<210> SEQ ID NO 3
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Amplification primer

<400> SEQUENCE: 3
cacgcgatgg catgtcaact ca                                              22

<210> SEQ ID NO 4
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Amplification primer

<400> SEQUENCE: 4
cctttctccg ccccgcacct gt                                              22

<210> SEQ ID NO 5
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: Amplification primer

<400> SEQUENCE: 5
tggccctcga tagaccttca actcc                                           25

<210> SEQ ID NO 6
<211> LENGTH: 22
<212> TYPE: DNA
<213> ORGANISM: Artificial Sequence
```

```
<220> FEATURE:
<221> NAME/KEY: misc_feature
<222> LOCATION: (1)..(22)
<223> OTHER INFORMATION: Amplification primer

<400> SEQUENCE: 6
cacgcgatgg catgtcaact ca                                              22
```